June 14, 1960 R. S. MOORE Plant Pat. 1,951
MINIATURE ROSE PLANT
Filed Aug. 21, 1959
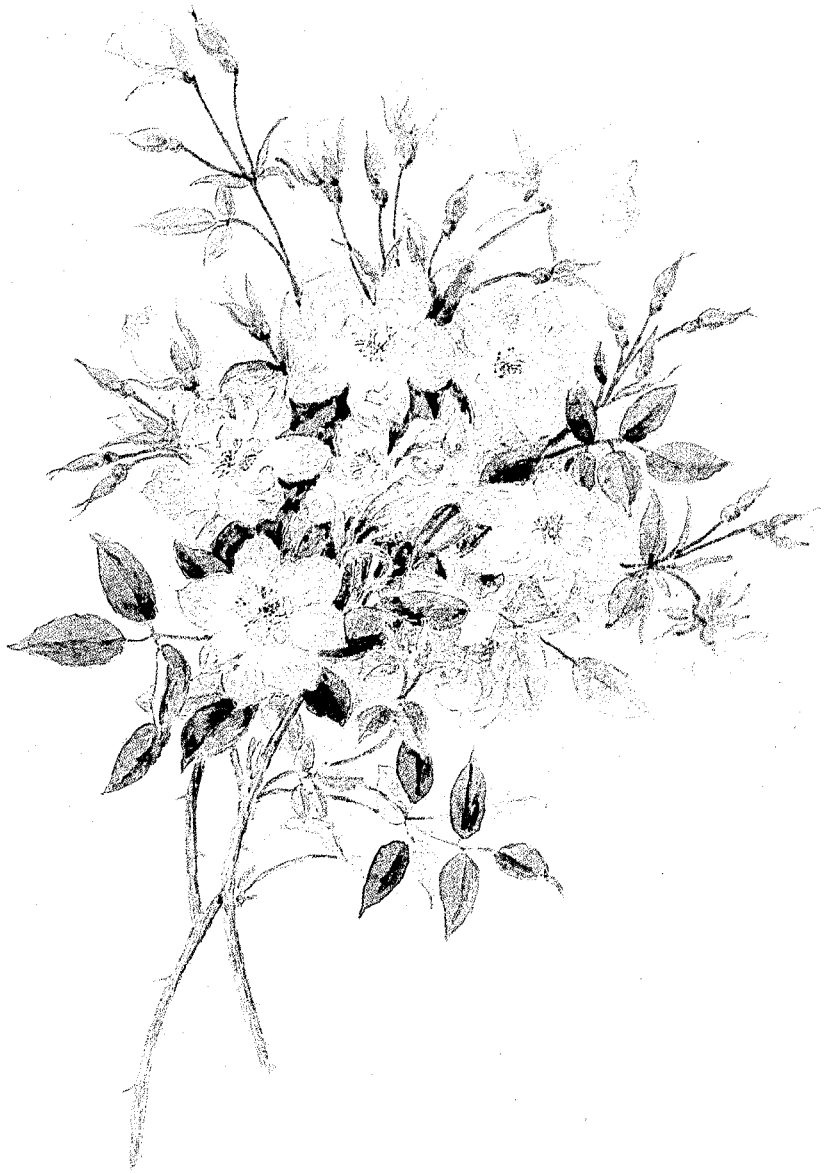
WITNESS
Addison E. Avery
INVENTOR
Ralph S. Moore
Webster & Webster
ATTYS.

United States Patent Office

Plant Pat. 1,951
Patented June 14, 1960

1,951

MINIATURE ROSE PLANT

Ralph S. Moore, 2519 E. Mineral King, Visalia, Calif.

Filed Aug. 21, 1959, Ser. No. 835,381

1 Claim. (Cl. 47—61)

This invention relates to a new and distinct variety of miniature rose plant of climbing type which bears semi-double flowers having golden stamens and variegated pink petals; i.e., the petals are a delicate shade of pink striped with white and shading to substantially full white at the base. The variety is the only known miniature rose having flowers with petals of such variegated color, and which is an outstanding and attractive characteristic.

The variety generally resembles the Pink Cameo rose (United States Plant Patent No. 1,451) in habit of growth and bloom, but—in comparison—bears flowers which are not as double, and which have the distinctive variegated color above described.

Additionally, the present variety of miniature rose plant blooms in loose clusters of three to five and in sprays up to twenty or more buds or flowers; the plant initially blooming when very small, and in maturity will grow—pillar type—to three or four feet tall if supported by a stake or trellis. The plant blooms almost constantly from the spring through the fall, with the bloom continuing in the winter if in a glass house.

The variety was originated by me, in my nursery located at Visalia, California, and under conditions of careful control and observation, as a cross between an unnamed seedling (red pillar type and unpatented) as the seed parent, and Zee (unpatented) as the pollen parent.

Subsequent to origination of the variety I successfully asexually reproduced it, in my nursery located as aforesaid, by cuttings; the reproductions having run true in all respects, and in no instance has there been a reversion of flowers from variegated to solid color.

The figure of the drawing illustrates a spray, including foliage, buds, and flowers.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Dwarf; climbing—pillar; seedling; cut flowers; garden decoration.

Class: Hybrid; climbing miniature.

*Flowers*

Continuity: Substantially continuous spring through fall, and winter in glass house.

Fragrance: Slight.

Flowers borne: Several to stem in irregular rounded cluster on normal strength, medium length stems.

Quantity of bloom: Free, both outdoors and in greenhouse.

Bud:

*Peduncle.*—Medium length; slender; erect. Numerous, very small red hairs. Color—medium green.

*Before calyx breaks.*—Size—small. Form—long; pointed, without foliaceous appendages on the surface of the bud, and with foliaceous parts and extending beyond the tip of the bud equal to one-half of its length. Color—medium green.

*As calyx breaks.*—Color—Pink to rose pink.

*As first petal opens.*—Size—small. Form—long; pointed. Color: outside—pink to rose pink, shading to white at base; inside—relatively deep rose (Tyrian Rose 24/1 British Colour Council) with white streaks or stripes, shading to white, and then to soft yellow, at base. Opening—opens well in all weather.

Bloom:

*Size when fully open.*—Small, averaging 1¼" to 1½".

*Petalage.*—Semi-double, with from ten to fifteen petals.

*Form.*—Flat; open; slightly cupped at tip.

Petals: Thick; satiny both inside and outside.

*Shape.*—Lanceolate.

*Color.*—Newly opened flower from plant grown outdoors—all petals: outside surface—Tyrian rose (24/2 British Colour Council), shading to near white at base; inside surface—Tyrian Rose (24/1 to 24/2 British Colour Council), with white stripes. A flower that was open for three days outdoors—all petals: outside surface—Persian rose (628/3 British Colour Council), shading to near white at base; inside surface—Persian rose 628/2 British Colour Council), with white stripes.

*General color effect.*—Newly opened flower—deep pink with white stripes, shading to white at base. Three days open—lighter pink with white stripes, shading to white at base.

*Behavior.*—Drop off cleanly.

*Flower longevity.*—Bush in garden—three to five days. Cut flowers kept at room temperatures—three to four days.

*Reproductive organs*

Stamens: Many; arranged irregularly; mixed sometimes with three to five petaloids. Color—golden.

Filaments: Medium length; most with anthers. Color—yellow.

Anthers: Medium size; all open at once. Color—yellow.

Pollen: Moderate. Color—yellow.

Pistils: Medium number.

Styles: Uneven; short; medium; loosely bunched.

Stigma: White.

Ovaries: All enclosed in calyx.

Hips: Ovoid. Color—reddish. Smooth; walls thin, fleshy.

Sepals: Long; straight; spear shaped. Color—green, becoming brown.

Seeds: Very few; large; usually only one per hip.

*Plant*

Foliage:

*Leaves.*—Compound of five to seven leaflets; normal abundance; moderately small; moderately heavy.

*Leaflets.* — Shape — lanceolate, with apex acute. Base—round. Margin—serrate.

*Color.*—Mature leaves: upper surface — normal green (22–K–7 Maerz and Paul); under surface —Lighter normal green (21–D–6 Maerz and Paul). Young leaves: upper surface—normal green; under surface—normal green with red tint.

*Rachis.*—Medium. Upper side—smooth, grooved, few short hairs; under side—thorny, three to four.

*Stipules.*—Medium length; narrow, with long points turning out at an angle of about 45 degrees.

Growth:

*Habit.*—Climbing; much branched.

*Growth.*—Vigorous.

*Canes.*—Medium.

*Main stems.*—Color—green. Thorns—several; medium length; hooked downward, with long narrow base. Prickles—none. Hairs—none.

*Branches.*—Color—green (18–L–8 Maerz and Paul). Thorns—several; medium length; hooked downward, with long narrow base; color—light brown (4–A–11 Maerz and Paul). Prickles—none. Hairs—none.

*New Shoots.*—Color—green, sometimes tinted bronze red. Thorns—several; medium length; long narrow base. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of vigorous, much branched miniature rose plant of climbing-pillar type, substantially as described and illustrated, which freely bears small, semi-double flowers with golden stamens and variegated pink petals striped with white and shading to substantially full white at the base; the plant generally resembling the Pink Cameo rose in habit of growth and bloom, but—in comparison—bearing flowers which are not so double and which are variegated pink instead of full pink; and further characterized by blooming in loose clusters of three to five and in sprays of up to twenty or more buds and flowers, by initial blooming when very small, by growth to three or four feet tall at maturity, and by blooming almost constantly from the spring through the fall, with the bloom continuing in winter if in a glass house.

No references cited.